(12) United States Patent
Bonelli et al.

(10) Patent No.: US 10,076,455 B2
(45) Date of Patent: Sep. 18, 2018

(54) METHOD FOR PRODUCING A BACKSHEET FOR ABSORBENT SANITARY ARTICLES AND AN ABSORBENT SANITARY ARTICLE INCLUDING THIS BACKSHEET

(71) Applicant: Fameccanica.Data S.p.A., Pescara (IT)

(72) Inventors: Guido Bonelli, Pescara (IT); Diego Gualtieri, Sulmona (IT)

(73) Assignee: FAMECCANICA.DATA S.P.A., Pescara (IT)

( * ) Notice: Subject to any disclaimer, the term of this patent is extended or adjusted under 35 U.S.C. 154(b) by 456 days.

(21) Appl. No.: 14/931,589

(22) Filed: Nov. 3, 2015

(65) Prior Publication Data
US 2016/0128878 A1 May 12, 2016

(30) Foreign Application Priority Data
Nov. 6, 2014 (IT) .............. TO2014A0918

(51) Int. Cl.
*B29C 65/02* (2006.01)
*A61F 13/62* (2006.01)
(Continued)

(52) U.S. Cl.
CPC ........ *A61F 13/627* (2013.01); *A44B 18/0011* (2013.01); *A61F 13/15723* (2013.01);
(Continued)

(58) Field of Classification Search
CPC ..... A44B 18/0011; B32B 5/26; A61F 13/627; Y10T 156/1077; Y10T 156/1097
(Continued)

(56) References Cited

U.S. PATENT DOCUMENTS 5,611,791 A 3/1997 Gorman et al.
5,900,101 A 5/1999 Justmann
(Continued)

FOREIGN PATENT DOCUMENTS

| EP | 2145555 A1 | 1/2010 |
|---|---|---|
| EP | 2540272 A1 | 1/2013 |
| EP | 2636782 A1 | 9/2013 |

OTHER PUBLICATIONS

Italian Search Report and Written Opinion dated Jul. 22, 2015 for Application No. TO2014A000918.

*Primary Examiner* — Scott W Dodds
(74) *Attorney, Agent, or Firm* — Patterson & Sheridan, LLP

(57) ABSTRACT

A method for producing a backsheet for absorbent sanitary articles provided with hook-and-loop fasteners, comprising the steps of: advancing a continuous web of fibrous material without support at a first speed, cutting the continuous web of fibrous material in a transverse direction so as to form sections of fibrous material, accelerating the sections of fibrous material at a second speed greater than said first speed, welding said sections of fibrous material spaced apart at constant intervals onto a continuous non-woven support web advancing at said second speed, so as to convert said sections of fibrous material into frontal tapes of loop-material for hook-and-loop fasteners, and fixing a continuous impermeable film to said continuous non-woven support web with said frontal tapes of loop-material, so as to form a continuous backsheet web provided with frontal tapes of loop-material spaced apart at constant intervals.

4 Claims, 2 Drawing Sheets

(51) Int. Cl.
*B32B 5/26* (2006.01)
*A44B 18/00* (2006.01)
*A61F 13/15* (2006.01)
*A61F 13/56* (2006.01)
*B29C 65/48* (2006.01)
*B29C 65/08* (2006.01)

(52) U.S. Cl.
CPC .... *A61F 13/15756* (2013.01); *A61F 13/5633* (2013.01); *A61F 13/62* (2013.01); *A61F 13/622* (2013.01); *B29C 65/48* (2013.01); *B32B 5/26* (2013.01); *B29C 65/08* (2013.01); *Y10T 156/1077* (2015.01)

(58) Field of Classification Search
USPC .......................................................... 156/265
See application file for complete search history.

(56) References Cited

U.S. PATENT DOCUMENTS

| | | | | |
|---|---|---|---|---|
| 6,022,430 | A * | 2/2000 | Blenke | A61F 13/15601 156/259 |
| 6,544,375 | B1 * | 4/2003 | Schmitz | A61F 13/15593 156/264 |
| 2006/0237116 | A1 * | 10/2006 | Willing | A61F 13/15756 156/73.1 |
| 2008/0260989 | A1 | 10/2008 | Lester et al. | |

* cited by examiner

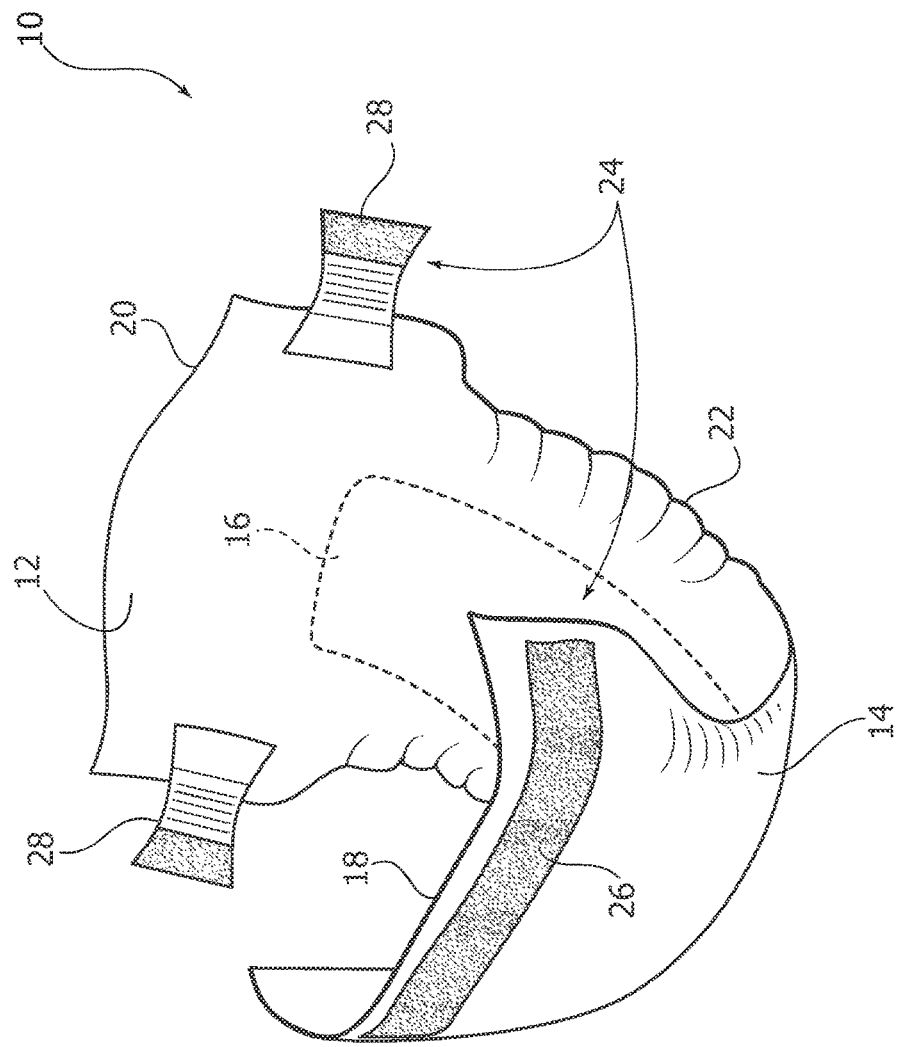

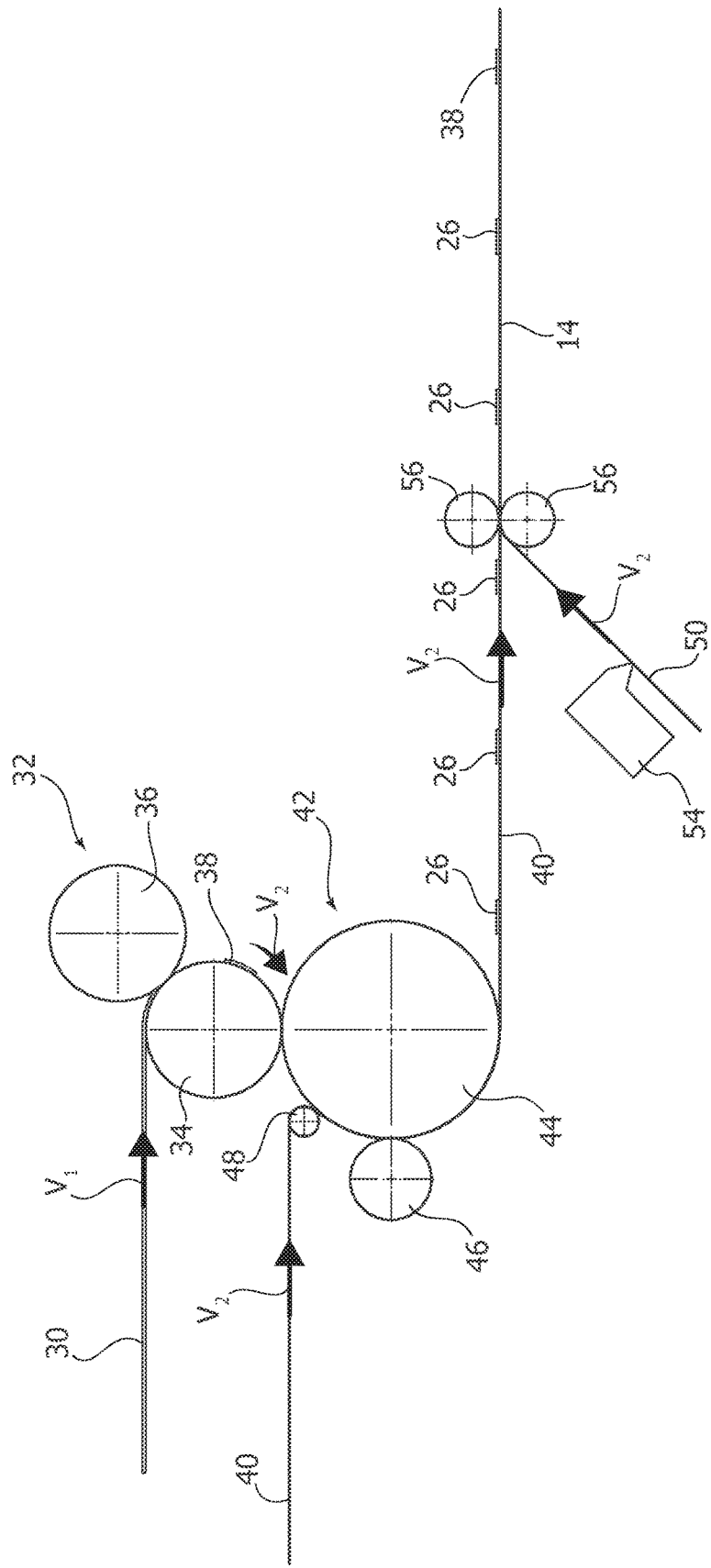

METHOD FOR PRODUCING A BACKSHEET FOR ABSORBENT SANITARY ARTICLES AND AN ABSORBENT SANITARY ARTICLE INCLUDING THIS BACKSHEET

CROSS-REFERENCE TO RELATED APPLICATIONS

This application claims benefit of Italian patent application number TO2014A000918, filed Nov. 6, 2014, which is herein incorporated by reference.

BACKGROUND OF THE INVENTION

Field of the Invention

The present invention relates to the production of absorbent sanitary articles, such as diapers, and relates to a method for producing a backsheet for absorbent sanitary articles. The invention also relates to an absorbent sanitary article including this backsheet.

Description of Prior Art

A diaper is normally composed of a permeable topsheet intended to come into contact with the user's skin when the diaper is worn, an impermeable backsheet and an absorbent core enclosed between the topsheet and the backsheet. Diapers normally have a back waist region and a front waist region that are closed around the user's waist by means of hook-and-loop fasteners, better known as Velcro© fastening devices. These fastening devices normally comprise a pair of closing wings that protrude laterally from the back waist region and which are releasably anchorable to a frontal tape applied on the outside of the backsheet at the front waist region. The frontal tape comprises a layer of loop-material forming the female part of the hook-and-loop closing device.

The loop-material of a hook-and-loop fastener is formed of a material, for example polypropylene, provided on an upper surface with micro-loops suitable for engaging with micro-hooks of the closing wings. The loop-material is normally fixed to a support typically consisting of a film of plastic material or of a non-woven polypropylene or the like.

EP-A-2540272 describes a multi-layer material for front panels of diapers, comprising a support formed of a polyolefinic film and a layer of loop-material formed by a non-woven polyolefinic material. The support and the layer of loop-material are secured together by glue.

In conventional solutions, the frontal tape formed of the loop-material and the respective support is cut and is applied to the outside of the backsheet level with the front waist region. The frontal tape is applied to the backsheet by means of glue or by ultrasound welding. Welding is generally not suitable because it can compromise the impermeability of the backsheet.

The backsheet of a diaper is a multi-layer composite structure including an impermeable film inside and a layer of outer non-woven material applied to the impermeable film by means of a layer of glue. In these cases, the frontal tape is applied on the outside of the non-woven layer of the backsheet, usually by means of a layer of glue. A drawback of this known solution is that the backsheet results in being rather thick and rigid at the frontal tape, given that in this area, the following are provided: an impermeable layer within the backsheet, a first layer of glue, an outer non-woven layer of the backsheet, a second layer of glue, the support of the frontal tape, a third layer of glue and the loop-material of the frontal tape.

In principle, it is possible to choose a material with preformed loops, similar to the "loop"-material of a Velcro® closure. A preformed loop-material for use in disposable articles can be of the type described in U.S. Pat. No. 5,611,791 by 3M, which describes a relatively thin nonwoven material that is corrugated to have the loop-structure. This material is ready to be applied, typically with an adhesive layer, to the backsheet. This solution, however, would be very expensive for disposable items.

EP 2636782 A1 by Aplix Inc. describes a non-woven composite material forming a loop-material for a hook-and-loop closure. A fibrous material is laminated to a substrate. The fibrous material becomes a loop-material after welding of the precursor fibrous material to the substrate. The welding is carried out in areas with a pattern that has the dual purpose of creating three-dimensionality in the surface of the precursor, making it suitable for engaging with the hooks, and of stabilizing it, so that the hooks do not tear the fibers when loaded.

SUMMARY OF THE INVENTION

The present invention aims to provide a method for producing a backsheet for absorbent sanitary articles and an absorbent sanitary article including this backsheet, which overcome the problems of the prior art.

According to the present invention, this object is achieved by a method having the characteristics forming the subject of claim 1 and by an absorbent sanitary article having the characteristics forming the subject of claim 4.

BRIEF DESCRIPTION OF THE DRAWINGS

The present invention will now be described in detail with reference to the attached drawings, given purely by way of non-limiting example, wherein:

FIG. 1 is a perspective view of an absorbent sanitary article according to the present invention.

FIG. 2 is a schematic side view of a method according to the present invention for producing a backsheet for absorbent sanitary products.

DETAILED DESCRIPTION

With reference to FIG. 1, numeral 10 indicates a diaper illustrated in the configuration in which it is worn. The diaper 10 comprises a topsheet 12 made of permeable material which, in use, is in contact with the user's skin, an impermeable backsheet 14 and an absorbent core 16 enclosed between the topsheet 12 and the backsheet 14. The diaper 10 has a front waist region 18 and a back waist region 20 which, in use, are closed around the user's waist. Between the front waist region 18 and the back waist region 20 a groin region 22 extends which, in use, is arranged between the legs of the user.

The diaper 10 comprises a hook-and-loop fastening device 24 to fasten the front waist region 18 and the back waist region 20 to each other. The hook-and-loop fasteners 24 comprise a frontal tape of loop-material 26 applied to the outer surface of the backsheet 14 in the front waist region 18 and a pair of closing wings 28, which protrude laterally from the back waist region 20. The closing wings 28 have a surface provided with micro-hooks forming the male part of the hook-and-loop fasteners 24. The frontal tape 26 has an outer surface provided with micro-loops that form the female part of the hook-and-loop fasteners 24.

FIG. 2 schematically illustrates a method for producing the backsheet 14 with its relative frontal tape 26.

Numeral 30 indicates a continuous web of fibrous material, forming a precursor of a loop-material for a hook-and-loop closure. The continuous web of fibrous material 30 is formed of a single non-woven layer of, for example polyester or polypropylene. The continuous web of fibrous material can be constituted of a single non-woven layer with longitudinally-oriented fibers, for example, a carded non-woven material. The continuous web of fibrous material 30 is made to advance in a rectilinear direction at a speed V1 towards a cutting unit 32. The cutting unit 32 comprises a cut-and-slip roller 34 and a knife roller 36 cooperating with the cut-and-slip roller 34. The cutting unit 32 carries out cutting of the continuous web of fibrous material 30 in a cross-sectional direction, so as to separate successive sections of fibrous material 38 from the continuous web 30 of fibrous material, which each form a precursor of a frontal tape of loop-material 26. The sections of fibrous material 38 are held on the surface of the cut-and-slip roller 34 by means of aspiration and are accelerated from the roller 34 at a speed $V_2$ that is greater than the speed $V_1$ of the continuous web of loop-material 30.

A continuous non-woven support web 40 is fed, at a speed $V_2$, towards a welding unit 42. The welding unit 42 comprises an anvil roller 44, a welding roller 46 and a deviating roller 48. The anvil roller 44 picks up the sections of fibrous material 38, by means of aspiration, from the cut-and-slip roller 34. The anvil roller 44 rotates with a peripheral speed equal to the speed $V_2$. The continuous non-woven support web 40 is fed onto the surface of the anvil roller 44 downstream of the welding roller 46. The welding roller 46 carries out the welding of the sections of fibrous material 38 onto the continuous non-woven web 40 at constant intervals.

The fibers of the sections of fibrous material 38 are fixed by means of thermal or ultrasound welding to the continuous non-woven support 40 with a pattern of welding areas that provides continuous lines, or rectilinear segments or curves, or points, or closed contours such as circles, of suitable dimensions, as illustrated for example in the already cited EP 2636782 A1. These welding areas form arcs of fibers arranged between two neighboring welding areas. These arcs form the loops suitable for receiving the hooks of a complementary element of a hook-and-loop closure. In a preferred embodiment of the present invention, in which the fibers of the continuous web of fibrous material 30 are preferably oriented longitudinally, the welding areas are formed of transversely-arranged continuous lines or segments, straight or curved. The welds, preferably transversal, therefore convert the sections of fibrous material 38, preferably with longitudinally-oriented fibers, into frontal tapes of loop-material 26.

At the outlet of the anvil roller 44, the continuous non-woven support web 40 has a continuous succession of frontal tapes of loop-material 26 fixed at regular intervals on one of its upper surfaces. The continuous non-woven support web 40 with frontal tapes of loop-material 38 advances at a speed $V_2$.

The continuous non-woven support web 40 with frontal tapes of loop-material 38 is coupled to a continuous impermeable film 50 which advances at a speed $V_2$. The continuous impermeable film 50 is applied on a surface of the continuous non-woven support web 40 opposite to the surface on which the frontal tapes of loop-material 26 are applied. The continuous impermeable film 50 and the continuous non-woven support web 40 are fixed together by means of a layer of glue applied by a glue-applying unit 54.

Downstream of the glue-applying unit 54, the continuous non-woven web 40 with the frontal tapes of loop-material 26 and the continuous impermeable film 50 are made to pass through a pair of pressure rollers 56.

Downstream of the pressure rollers 56, a continuous backsheet web 14 is formed, provided with frontal tapes of loop-material 26, spaced apart at regular intervals, which advances at a speed $V_2$. In subsequent steps of the process, the continuous backsheet web 14 is continuously coupled to other components to form a continuous chain of blanks of diapers according to known techniques.

Each backsheet 14 is formed of an impermeable film 50 fixed to a support layer of non-woven material 40 provided with a frontal tape of loop-material 26 without support. The frontal tape of loop-material 26 without support is fixed directly to the non-woven support layer 40, without any direct fixing to the impermeable film 50.

The application of the sections of fibrous material 38 onto the continuous non-woven support web 40 before applying the continuous non-woven support web 40 to the continuous impermeable film 50 is advantageous because it does not compromise the integrity of the continuous impermeable film 50.

The invention consists of the application of the fibrous material precursor of the loop-material directly onto the non-woven material intended to form the support of the backsheet, which therefore acts as a substrate of the frontal tape of loop-material. The application of the fibrous material occurs by means of thermomechanical or ultrasound welding that "activates" the precursor material. Subsequently, the non-woven material with the "activated" precursor material is laminated to the impermeable film, typically by means of adhesive, to form the composite backsheet already comprising the loop-material. The activation of the precursor material by means of welding to the substrate is carried out directly onto the support web of the backsheet. In this way, it is possible to dispense with the substrate of the frontal tape. Thanks to this solution, it is not necessary to acquire an expensive loop-material, but a simple and economic non-woven material is sufficient, preferably with longitudinally-arranged fibers, which will become a loop-material by means of in-line welding onto the support web of the backsheet, in a particularly preferred way with transversal welds coupled to the non-woven material with longitudinally-arranged fibers.

It is understood that the present invention enables the support layer to be avoided, which, in the solutions according to the prior art is arranged between the layer of loop-material and the outer surface of the backsheet. Therefore, the present invention allows the obtainment of diapers with a reduced thickness and a greater flexibility at the frontal tape. The invention also allows a considerable reduction of the cost of the frontal tape of loop-material.

Of course, without prejudice to the principle of the invention, the details of construction and the embodiments can be widely varied with respect to those described and illustrated without thereby departing from the field of the invention as defined by the following claims.

The invention claimed is:

1. A method for producing a backsheet for absorbent sanitary articles provided with hook-and-loop fasteners, comprising the steps of:
   advancing a continuous web of fibrous material without support at a first speed;
   cutting the continuous web of fibrous material without support in a transverse direction so as to form sections of fibrous material;

accelerating the sections of fibrous material at a second speed greater than said first speed;

welding said sections of fibrous material spaced apart at constant intervals onto a continuous non-woven support web advancing at said second speed, so as to convert said sections of fibrous material into frontal tapes of loop-material for hook-and-loop fasteners; and fixing a continuous impermeable film to said continuous non-woven support web with said frontal tapes of loop-material, so as to form a continuous backsheet web provided with frontal tapes of loop-material spaced apart at constant intervals.

2. A method according to claim 1 wherein said continuous web of fibrous material without support comprises a material with longitudinally-oriented fibers.

3. A method according to claim 1, wherein the welding of said sections of fibrous material to said continuous non-woven support web is carried out by means of welding lines arranged in a transverse direction.

4. A method according to claim 1, wherein the fixing of the continuous impermeable film to said continuous non-woven support web with said frontal tapes of loop-material is carried out by gluing.

\* \* \* \* \*